US009226886B2

(12) United States Patent
Lee et al.

(10) Patent No.: US 9,226,886 B2
(45) Date of Patent: Jan. 5, 2016

(54) METHOD FOR MANUFACTURING A COSMETIC BIO-CELLULOSE MASK PACK SHEET AND USE THEREOF

(75) Inventors: Chang Keun Lee, Gyeonggi-do (KR); Kuan Chi Hsu, Gyeonggi-do (KR); Jun Cheol Cho, Gyeonggi-do (KR); Youn Joon Kim, Gyeonggi-do (KR); Sang Hoon Han, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/881,967

(22) PCT Filed: Oct. 25, 2011

(86) PCT No.: PCT/KR2011/007950
§ 371 (c)(1), (2), (4) Date: May 28, 2013

(87) PCT Pub. No.: WO2012/057486
PCT Pub. Date: May 3, 2012

(65) Prior Publication Data

US 2013/0244977 A1 Sep. 19, 2013

(30) Foreign Application Priority Data

Oct. 26, 2010 (KR) ........................ 10-2010-0104511

(51) Int. Cl.

| | |
|---|---|
| ***C12P 19/04*** | (2006.01) |
| ***C12N 1/20*** | (2006.01) |
| ***A61K 8/73*** | (2006.01) |
| ***A45D 44/00*** | (2006.01) |
| ***A61K 8/02*** | (2006.01) |
| ***A61K 8/97*** | (2006.01) |
| ***A61Q 19/08*** | (2006.01) |
| ***A61K 8/99*** | (2006.01) |

(52) U.S. Cl.
CPC .............. *A61K 8/731* (2013.01); *A45D 44/002* (2013.01); *A61K 8/0212* (2013.01); *A61K 8/97* (2013.01); *A61K 8/99* (2013.01); *A61Q 19/08* (2013.01); *C12P 19/04* (2013.01); *A61K 2800/85* (2013.01)

(58) Field of Classification Search
USPC .............................................. 435/101, 252.1
IPC .................................... C12P 19/04; C12N 1/20
See application file for complete search history.

(56) References Cited

U.S. PATENT DOCUMENTS

2004/0161435 A1* 8/2004 Gupta ........................... 424/401
2009/0041815 A1* 2/2009 Legendre ...................... 424/401

FOREIGN PATENT DOCUMENTS

FR 2916971 A1 * 12/2008

OTHER PUBLICATIONS

George et al. Physico-Mechanical Properties of Chemically Treated Bacterial (Acetobacter Xylinum) Cellulose Membrane; World Journal of Microbiology & Biotechnology, vol. 21 (2005) pp. 1323-1327.*

Krystynowicz et al. Factors Affecting the Yield and Properties of Bacterial Cellulose; Journal of Industrial Microbiology & Biotechnology, vol. 29 (2002) pp. 189-195.*

Pa'e et al. Modified Fermentation for Production of Bacterial Cellulose/Polyaniline As Conductive Biopolymer Material; Jurnal Teknologi, vol. 62, No. 2 (2013) pp. 21-23.*

International Search Report for PCT/KR2011/007950, mailed Oct. 25, 2011.

* cited by examiner

*Primary Examiner* — Kagnew H Gebreyesus
*Assistant Examiner* — Paul Martin
(74) *Attorney, Agent, or Firm* — Nixon & Vanderhye P.C.

(57) ABSTRACT

The present invention relates to a mask pack sheet using bio-cellulose obtained from fermented ginseng extracts, and more particularly, to a method for manufacturing a cosmetic mask pack sheet, comprising injecting microbial strains into a culture medium containing ginseng extracts so as to ferment the ginseng extracts and prepare a bio-cellulose sheet, and dipping the sheet into a cosmetic liquid.

3 Claims, No Drawings

METHOD FOR MANUFACTURING A COSMETIC BIO-CELLULOSE MASK PACK SHEET AND USE THEREOF

This application is the U.S. national phase of International Application No. PCT/KR2011/007950, filed 25 Oct. 2011, which designated the U.S. and claims priority to KR Application No. 10-2010-0104511, filed 26 Oct. 2010, the entire contents of each of which are hereby incorporated by reference.

TECHNICAL FIELD

The present invention relates to a cosmetic mask pack sheet comprising a bio-cellulose obtained by fermenting a ginseng extract and to a method for producing bio-cellulose which can be used as a mask pack sheet.

BACKGROUND ART

Generally, a sheet-type mask pack in the cosmetic field is a face-shaped sheet product which can exhibit moisturizing and cleansing effects when applied to a face without the need to apply cosmetic lotion with hand. Examples of sheet-type mask packs, which are on the market, include a sheet designed to completely cover a face, a composite sheet comprising an upper sheet and a lower sheet, and sheets conforming to specific portions, including the portion under the eye, the eye rims, and the sides of the mouth. The sheet-type mask pack has a support in which an emulsion can be impregnated so as to act on the skin for a longer period of time than general cosmetic emulsions. Also, the occlusive effect of the support increases the skin penetration of a skin active ingredient, and thus the sheet-type mask pack has excellent effects on improvements in skin moisturization and conditions.

In this cosmetic mask pack sheet, a nonwoven fabric made of either plant cellulose fiber (derived mainly from cotton or pulp) or synthetic fiber is generally used not only as an element in which a cosmetic emulsion is impregnated, but also a mask-shaped support. The touch feeling and effect of the cosmetic mask pack sheet may vary depending on the material or kind of nonwoven fabric. In addition to fiber nonwoven fabric, supports made of various and unique materials may be used to support the cosmetic emulsion in the cosmetic mask pack sheet. Furthermore, studies on various materials have been conducted to improve the touch feel, wearing feel and effect of the cosmetic mask pack sheet.

Meanwhile, cellulose produced by microbial culture is known as bio-cellulose or microbial cellulose and is used as a material for a medical burn-treating agent or a cosmetic mask pack. The production of general bio-cellulose is mainly performed by microbial culture in a fruit juice medium. Microbial strains that produce bio-cellulose include *Acetobacter* sp., *Rhizobium* sp., and *Agrobacterium* sp. Among them, *Acetobacter* sp. has the highest production yield, and *Acetobacter xylinum* is the most well-known microorganism among members of *Acetobacter* sp. (see Korean Patent No. 0405776). In addition, in an attempt to increase the production yield of bio-cellulose, Korean Patent Laid-Open Publication No. 2002-0067226 discloses a method for producing bio-cellulose, the method comprising stationary- or shake-culturing a mixture of an *Acetobacter* sp. microorganism, which produces bio-cellulose, and a lactic acid microorganism which produces bacteriocin for preventing microbial contamination.

Bio-cellulose is a polymer material produced by the culture of various kinds of bacteria, particularly an *Acetobacter* sp. strain and is produced in a pellicle form in a culture medium under stationary culture conditions (see GB Patent No. 2131701). Bio-cellulose is a polymer having β-1,4-bonded glucose, like plant-derived cellulose, but it has a fiber width significantly smaller than that of plant-derived cellulose and has a three-dimensional network structure. Thus, bio-cellulose has a high ability to retain water and can give a soft touch feeling and a smooth wearing feeling, like a hydrogel mask. Accordingly, bio-cellulose is highly industrially applicable compared to plant-derived cellulose. Also, in order to apply produced bio-cellulose as a cosmetic sheet mask, the death of microorganisms injected for fermentation and the removal of medium should be essentially carried out. For this purpose, efficient processes are required to be applied for the manufacture of a sheet mask after culture.

Ginseng is a well-known oriental herb and is widely used in Chinese medicine, the health industry field and the cosmetic field. Various studies on the effects of ginsenosides (typical components of ginseng) on skin cells have been conducted, and particularly, it was reported that ginsenosides activate the production of hyaluronic acid in the human body by increasing the expression of hyaluronic acid synthase (HAS) in human cells (Biochem. Biophys. Res. Commun. 316 (2004) 348-355). Thus, it was found that ginsenosides of ginseng have very excellent skin beauty effects, including anti-aging, antioxidant and anti-inflammatory activities in skin cells. In order to use such skin beauty effects, various types of products comprising ginsenosides have been developed and applied.

DISCLOSURE

Technical Problem

Accordingly, in order to use bio-cellulose as a cosmetic mask pack sheet, the present inventors have conducted extensive studies to impart additional effects to bio-cellulose in addition to water-holding capacity and touch feeling, and as a result, have found that, when a medium for producing bio-cellulose contains a ginseng extract in place of fruit juice, skin beauty effects can be additionally imparted to bio-cellulose, thereby completing the present invention.

Therefore, it is an object of the present invention to provide a cosmetic mask pack sheet comprising a bio-cellulose fermented using a ginseng extract and a manufacture method thereof.

Technical Solution

In order to accomplish the above object, the present invention provides a cosmetic mask pack sheet comprising a bio-cellulose prepared in a culture medium containing a ginseng extract.

The present invention also provides a method for manufacturing a cosmetic mask pack sheet, the method comprising the steps of: 1) inoculating a bio-cellulose-producing microbial strain into a culture medium containing a ginseng extract to produce bio-cellulose; and 2) killing the inoculated microbial strain and removing the culture medium.

Advantageous Effects

A cosmetic mask pack sheet comprising a bio-cellulose produced according to the present invention can be used as a new cosmetic mask sheet material which can provide skin beauty effects in addition to water-holding capacity and touch feeling.

BEST MODE

The present invention provides a method for producing bio-cellulose by microbially fermenting a ginseng extract in a culture medium and a cosmetic mask pack sheet comprising the produced bio-cellulose as a water-holding material and a support.

In order to use the bio-cellulose of the present invention as a cosmetic mask pack sheet, the present invention also provides a method for manufacturing a cosmetic sheet mask pack, the method comprising: inoculating microorganisms into a culture medium for fermentation; performing fermentation in the culture medium to obtain bio-cellulose; killing the microorganisms inoculated for fermentation, removing the culture medium, and dewatering the bio-cellulose; and impregnating a cosmetic emulsion into the bio-cellulose.

Hereinafter, the present invention will be described in further detail.

The bio-cellulose mask pack sheet of the present invention is manufactured by a method comprising the following steps:

1) inoculating a bio-cellulose-producing microbial strain into a culture medium containing a ginseng extract to produce bio-cellulose; and 2) killing the inoculated microbial strain and removing the culture medium.

The bio-cellulose of the present invention is produced using a culture medium containing a ginseng extract. Also, in the present invention, a culture medium containing a ginsenoside extracted from ginseng may be used. The kind of ginseng which can be used in the present invention is not specifically limited, and fresh ginseng, red ginseng, white ginseng, Taegeuk ginseng, or fine root ginseng may be used in the present invention. An extract from one or more of the above ginseng kinds may be used in the culture medium in the present invention. Preferably, an extract from white ginseng is used in the present invention.

In the present invention, in order to increase production efficiency, a plant extract containing glucose may be added to the culture medium containing the ginseng extract, and typical examples thereof include extracts from cocoa, corn, *Rubus coreanus* and the like. Also, acetic acid may be suitably added to adjust the pH of the microbial culture medium. The pH of the microbial culture medium is preferably in the range of 3-7, but can be suitably controlled according to the kind of microorganism inoculated.

The ginseng extract that is used in the present invention may be prepared according to any method known. in the art, and the preparation method is not specifically limited. For example, the ginseng extract may be prepared by finely cutting, crushing or powdering ginseng, extracting the ginseng pieces or powder with a suitable solvent, filtering the extract, and concentrating and drying the filtrate. Herein, the solvent may be one or more of ethanol, water, polyol and the like.

The culture medium that is used to produce bio-cellulose in the present invention contains the ginseng extract in an amount of 0.01 wt % or more based on the total weight of the culture medium, in addition, the culture medium may consist only of the ginseng extract. If the content of the ginseng in the culture medium is less than 0.01 wt %, it will be difficult to obtain. a cosmetic mask pack sheet showing a skin condition-improving effect.

The culture medium that is used to produce bio-cellulose in the present invention may contain no nitrogen source or may contain. various nitrogen sources together with the ginseng extract in order to improve the yield of bio-cellulose. The nitrogen source that is used in the present invention is not specifically limited, and specific examples thereof include yeast extracts, ammonium sulfate and the like.

Microorganisms which are used to produce bio-cellulose in the present invention include *Acetobacter* sp., *Rhizobium* sp., and *Agrobacterium* sp. In addition, a mixture of various kinds of microorganisms may be used in culture in the present invention in order to increase production efficiency. More preferably, the culture process is effectively carried out according to the method disclosed in Korean Patent Laid-Open Publication No. 2002-0067226, which comprises stationary- or shake-culturing a mixture of an *Acetobacter* sp. microorganism having a good production yield and a lactic acid microorganism which produces bacteriocin for preventing microbial contamination.

For the effective production of bio-cellulose, the bio-cellulose-producing strain that is used in the present invention is inoculated into the culture medium containing the ginseng extract after being precultured.

In order to obtain a design of the cosmetic mask pack sheet comprising bio-cellulose according to the present invention, a face-shape design may be intaglio-formed in a tray during culture to obtain bio-cellulose in a completed design form. On the other hand, a completed design may also be obtained by culturing bio-cellulose in a flat tray (e.g., square shape), and cutting the cultured bio-cellulose in a face shape using a knife.

In order for the bio-cellulose of the present invention to be used as a cosmetic mask pack sheet, materials other than bio-cellulose, such as the inoculated microorganisms and the culture medium, should be removed. Thus, a process for killing the inoculated microorganisms and removing the culture medium from the bio-cellulose is carried out. For this purpose, it is most effective to repeat a hot water sterilization process.

The cosmetic bio-cellulose mask pack sheet of the present invention is dewatered or dried. to a specific water content, before it is impregnated with a cosmetic emulsion. However, if the cosmetic bio-cellulose mask pack sheet is impregnated with cosmetic emulsion after complete drying, the water-holding capacity of the bio-cellulose will be reduced, and thus the swelling of the mask is time-consuming or insufficient. The most effective method to overcome this shortcoming dewatering process employing a centrifuge, wherein the water content of the bio-cellulose sheet is kept at 1-50 times (preferably 10-20 times) the dry weight of the bio-cellulose sheet, before a cosmetic emulsion is impregnated into the bio-cellulose sheet. If the water content of the bio-cellulose sheet is kept at less than one time the dry weight, the swelling of the bio-cellulose sheet will be time-consuming or insufficient, and thus the bin-cellulose sheet will not be sufficiently impregnated with a cosmetic emulsion and will not have a soft touch feeling. If the water content of the bio-cellulose sheet is more than 50 times the dry weight, the bio-cellulose sheet cannot be impregnated with a sufficient amount of a cosmetic emulsion, and thus cannot function as a cosmetic mask sheet.

MODE FOR INVENTION

Hereinafter, preferred examples will be described for a better understanding of the present invention. It is to be understood, however, that these examples are for illustrative purposes only and are not intended to limit the scope of the present invention.

Reference Example 1

Preparation of Ginseng Extract 30 kg of a mixed solvent of ethanol and water (1:1) was added to 1 kg of white ginseng which was then heated for 4 hours. The resulting material was allowed to stand at room temperature for 16 hours, after which it was purified with a 3M filter and stored. 100 g of the stored material was taken and the dry weight thereof was measured. Then, the ginseng extract was diluted with purified water to a concentration of 0.5%.

Reference Example 2

Culture of *Acetobacter xylinum*

First, *Acetobacter xylinum* BRC21, a cellulose-producing strain, was precultured.

*Acetobacter xylinum* BRC21 was cultured in a HS medium (20.00 g/l of glucose, 5.00 g/l of yeast extract, 2.70 g/l of sodium phosphate, and 1.15 g/l of citric acid) containing 2% glucose as a carbon source. Specifically, 50 ml of the HS medium was dispensed in a 250 ml Erlenmeyer flask and sterilized at 120° C. for 30 minutes, and then *Acetobacter xylinum* BRC21 was inoculated in the medium and cultured in an incubator at 30° C. for 38 hours.

Example 1

Production of Fermented Bio-Cellulose Using Ginseng Extract

Each of 0% (v/v), 10% (v/v), 20% (v/v) and 30% (v/v) of the ginseng extract was added to 20 g/l of glucose and 10 ml/l of acetic acid, and distilled water was added thereto to a volume of 1 liter. Then, 50 ml of each of the production media was dispensed in a 250 ml Erlenmeyer flask and sterilized at 120° C. for 30 minutes, after which 5 ml of the precultured *Acetobacter xylinum* BRC21 was inoculated in each medium and cultured in an incubator at 30° C. for 120 hours.

Example 2

Production of Bio-Cellulose Using Medium Containing Ginseng Extract and Ammonium Sulfate as Nitrogen Source In a manner similar to Example 1, each of 0% (v/v), 10% (v/v), 20% (v/v) and 30% (v/v) of the ginseng extract was added to 20 g/l of glucose and 10 ml/l of acetic acid, and 0.5 g/l of ammonium sulfate as a nitrogen source was added thereto, after which distilled water was added thereto to a volume of 1 liter. Then, 50 ml of each of the production media was dispensed in a 250 ml Erlenmeyer flask and sterilized at 120° C. for 30 minutes, after which 5 ml of the precultured *Acetobacter xylinum* BRC21 was inoculated in each medium and cultured in an incubator at 30° C. for 120 hours.

Test Example 1

Comparison of Production Yields of Microbial Celluloses

In order to compare the production yields of celluloses produced in Examples 1 and 2, the produced celluloses were recovered from the culture media. To remove protein components such as microbial cells from the cellulose masses, the cellulose materials were dipped in 1% NaOH aqueous solution and allowed to stand at room temperature for 24 hours, and then the cellulose materials were neutralized with 1% acetic acid solution. Then, the cellulose materials were sufficiently washed with water and dried. The weight of the dried material was weighed to determine the amount of cellulose produced, and the results are shown in Table 1 below.

TABLE 1

| Example | *Ginseng* extract content (% v/v) | Amount of cellulose produced (g/l) |
|---|---|---|
| 1 | 0 | 1.56 |
| | 10 | 3.46 |
| | 20 | 3.76 |
| | 30 | 4.16 |
| 2 | 0 | 1.83 |
| | 10 | 4.81 |
| | 20 | 4.87 |
| | 30 | 5.56 |

As can be seen in Table 1 above, as the content of the ginseng extract increased, the amount of cellulose produced also increased. In addition, when the nitrogen source was added, the amount of cellulose produced increased compared to when no nitrogen source was used.

Test Example 2

Examination of Whether Ginseng Component is Present in Mask Pack Sheet

In a manner similar to Example 1, 30% (v/v) of white ginseng extract was added to 20 g/l of glucose and 10 ml/l of acetic acid, and distilled water was added thereto. Then, 50 ml of the production media was dispensed in a 250 ml Erlenmeyer flask and sterilized at 120° C. for 30 minutes. 50 ml of the medium was selected for analysis, and 5 ml of the precultured *Acetobacter xylinum* BRC21 was inoculated in the medium and cultured in an incubator at 30° C. for 120 hours. In order to determine whether the produced cellulose contained a ginseng component, the produced cellulose was finely crushed, and 5 g of the crushed cellulose was concentrated and added to 1 ml of a solvent. The sample was crushed ultrasonically and centrifuged to separate the solution. The resulting material was purified using a syringe filter. The resulting sample was analyzed using Aligent 1200 HPLC and a 5 μm column at 30° C. and 203 nm. The results of the analysis are shown in Table 2 below.

TABLE 2

| Components | Analysis of *ginseng* | Example 1 (30% white ginseng) |
|---|---|---|
| Rc | 89.7472 | 7.1118 |
| Re | 334.1075 | N.D |
| Rg1 | 434.0580 | 4.0031 |
| Rg2 | 10.8078 | 6.6321 |
| Rh1 | 4.6561 | 2.4940 |
| Rh2 | 586.5 | N.D |
| Rd | 33.9693 | 4.5447 |
| Rb1 | 69.9510 | 3.5988 |
| Rb2 | 169.5753 | 3.3872 |

unit: PPM

N.D: not detected

As can be seen in Table 2 above, ginsenoside components detected in ginseng were also detected in the mask pack sheet, suggesting that ginsenosides in the culture medium containing the ginseng extract remain in the mask pack sheet even after fermentation so that they can act on the skin.

Reference Example 3

Sheet Mask Packs (Corresponding to Comparative Example 1 and Preparation Example 1)

An emulsion having the composition shown in Table 3 below was prepared.

TABLE 3

| | Raw material name | Content (wt %) |
|---|---|---|
| Components of oil part | Hydrogenated polydecene | 8.0 |
| | Dimethicone | 0.5 |
| | Glyceryl stearate SE/PEG-100 stearate | 0.8 |
| | Polyglyceryl-3 methyl glucose distearate | 1.0 |
| Components of water part | Purified water | Balance |
| | Disodium EDTA | 0.02 |
| | Glycerin | 5.0 |
| | Butylene glycol | 10.0 |
| | Preservative | 0.25 |
| | Triethanolamine | 0.05 |
| | Carbomer | 0.05 |
| | Fragrance | q.s. |

Method for Preparation of Emulsion (1) The components of the oil part were uniformly mixed by heating to 70~75° C.

(2) The components of the water part were uniformly dissolved and mixed by heating to 70~75° C.

(3) The mixture of step (1) was added slowly to the mixture of step (2) with stirring at a temperature of 70~75° C., and then cooled, thereby obtaining an oil-in-water emulsion.

The bio-cellulose prepared using 30% (v/v) of the ginseng extract in Example 1 was formed and cut in a face shape, and then impregnated with 20 g of the emulsion prepared using the composition of Table 3, thereby manufacturing a sheet mask pack of Preparation Example 1.

Meanwhile, a commercially available rayon nonwoven fabric was formed and cut in a face shape, and then impregnated with 20 g of the emulsion prepared using the composition of Table 3, thereby manufacturing a sheet mask pack of Comparative Example 1.

Test Example 3

Measurement of Improvement in Skin Elasticity of Human Body

The effects of the mask packs of Preparation Example 1 and Comparative Example 1 on an improvement in skin elasticity were measured. Thirty healthy women (over 30 years old) were selected and groups into two groups. Under the conditions of temperature of 24~26° C. and humidity of 75%, the cosmetic sheet mask packs of Preparation Example 1 and Comparative Example 1 were applied to the faces of the subjects of each group once a day for 4 weeks, and then the skin elasticity of each subject was measured using Cutometer SEM 575 (C+K Electronic Co., Germany). The results of the measurement are shown in Table 4 below. The results in Table 4 are described as ΔR8 (R8 (left)-R8 (right) of the Cutometer SEM 575, in which R8 means skin viscoelasticity. The Cutometer® Skin Elasticity Meter 575 is a non-invasive suction device providing a reliable measurement of skin elasticity.

TABLE 4

| Sample | Skin elasticity |
|---|---|
| Preparation Example 1 | 0.45 |
| Comparative Example 1 | 0.12 |

As can be seen in Table 4 above, the use of the sheet according to the present invention makes it possible to more effectively deliver the cosmetic composition to the skin so as to significantly improve skin elasticity.

Test Example 4

Evaluation of Touch Feeling and Satisfaction of Product

In order to evaluate the sheet mask packs of Preparation Example 1 and Comparative Example 1 with respect to the adhesion feeling and softness during use, the moist feeling after use and the overall satisfaction, 30 test subjects were selected, and the cosmetic sheet mask packs of Preparation Example 1 and Comparative Example 1 were alternately used, followed by a questionnaire. In the questionnaire, the preference of the two sheet mask packs was selected with respect to the adhesion feeling and softness during use, the moist feeling after use and the overall satisfaction. The results of the questionnaire are shown in Table 5 below.

TABLE 5

Comparison of effect on skin elasticity between Preparation Example 1 and Comparative Example 1

| | Adhesion feeling during use (persons) | Softness during use (persons) | Moist feeling after use (persons) | Overall satisfaction (persons) |
|---|---|---|---|---|
| Comparative Example 1 | 6 | 3 | 8 | 6 |
| Preparation Example 1 | 24 | 27 | 22 | 24 |

As can be seen from the results in Table 5 above, the mask pack of Preparation Example 1 comprising the bio-cellulose cultured in the ginseng extract had high satisfaction with respect to the adhesion feeling during use compared to the general rayon nonwoven fabric of Comparative Example 1. Moreover, the gel texture of the bio-cellulose sheet (Preparation Example 1) had high satisfaction with respect to softness compared to the general rayon nonwoven fabric made of fibers (Comparative Example 1). In addition, with respect to the moist feeling after use, which is the most important property of cosmetic sheet mask packs, the satisfaction of Preparation Example 1 comprising the bio-cellulose according to the present invention was higher. Also, with respect to the overall satisfaction, the bio-cellulose sheet according to the present invention was significantly higher.

The invention claimed is:

1. A method for manufacturing a cosmetic mask pack formed from a pellicle bio-cellulose sheet containing ginseng extract therein, the method comprising the steps of:

1) inoculating an *Acetobacter xylinum* BRC21 as a bio-cellulose-producing microbial strain into a culture medium containing an ammonium sulfate as a nitrogen source and an ethanol extract of white ginseng to produce bio-cellulose in pellicle form; wherein the ethanol extract is contained in an amount of at least 10 v/v % based on the total volume of the culture medium;

2) killing the inoculated microbial strain and removing the culture medium, and 3) forming the resulting bio-cellulose into a cosmetic pack sheet in which the ginsenosides contained in the ethanol extract remain in the sheet.

2. The manufacturing method of the cosmetic mask pack according to claim 1, wherein the ginseng extract is contained in an amount of 10 to 30 v/v % based on the total volume of the culture medium.

3. A method of delivering ginsenosides to the skin of a subject in need of same comprising topically applying a cosmetic mask pack sheet to the skin of said subject, wherein the cosmetic mask pack sheet is formed from a pellicle bio-cellulose sheet containing ginseng extract and formed by the steps of:

1) inoculating an *Acetobacter xylinum* BRC21 as a bio-cellulose-producing microbial strain into a culture medium containing an ammonium sulfate as a nitrogen source and an ethanol extract of white ginseng to produce bio-cellulose in pellicle form, wherein the ethanol extract is contained in an amount of at least 10 v/v % based on the total volume of the culture medium;

2) killing the inoculated microbial strain and removing the culture medium, and 3) forming the resulting bio-cellulose into a cosmetic pack sheet in which the ginsenosides contained in the ethanol extract, remain in the sheet.

* * * * *